United States Patent [19]

Heinz

[11] 3,935,726

[45] Feb. 3, 1976

[54] APPARATUS FOR MEASURING VISCOSITY OF LIQUIDS

[76] Inventor: Werner Heinz, Dabringhauserstr. 72, Cologne-Dellbruck, Germany

[22] Filed: June 17, 1974

[21] Appl. No.: 480,313

[30] Foreign Application Priority Data
June 18, 1973 Germany.............................. 2330964

[52] U.S. Cl. ..................................................... 73/60
[51] Int. Cl.² ......................................... G01N 11/00
[58] Field of Search ............ 73/59, 60, 54; 308/237, 308/238, DIG. 8

[56] References Cited
UNITED STATES PATENTS
| | | | |
|---|---|---|---|
| 2,703,066 | 3/1955 | Savins | 73/59 |
| 3,435,666 | 4/1969 | Fann | 73/59 |

FOREIGN PATENTS OR APPLICATIONS
| | | | |
|---|---|---|---|
| 288,632 | 4/1968 | Australia | 73/54 |

Primary Examiner—Houston S. Bell, Jr.
Assistant Examiner—Willis Little
Attorney, Agent, or Firm—Burns, Doane, Swecker & Mathis

[57] ABSTRACT

An improved apparatus is provided for measuring the viscosity of a liquid comprising a rotatable container means; means for rotating said container means at a desired speed; a freely rotatable member within said container means, said container means and said member defining a volume therebetween for receiving liquid to be measured; a third bath surrounding said container means for maintaining said container means at a desired constant temperature; means for measuring torque of said member when said volume is charged with liquid to be measured and said container means is rotated by said rotating means; and a bearing made from a material having a high thermal conductivity and located between and contacting said container means and said fluid bath to facilitate relative rotation therebetween.

15 Claims, 2 Drawing Figures

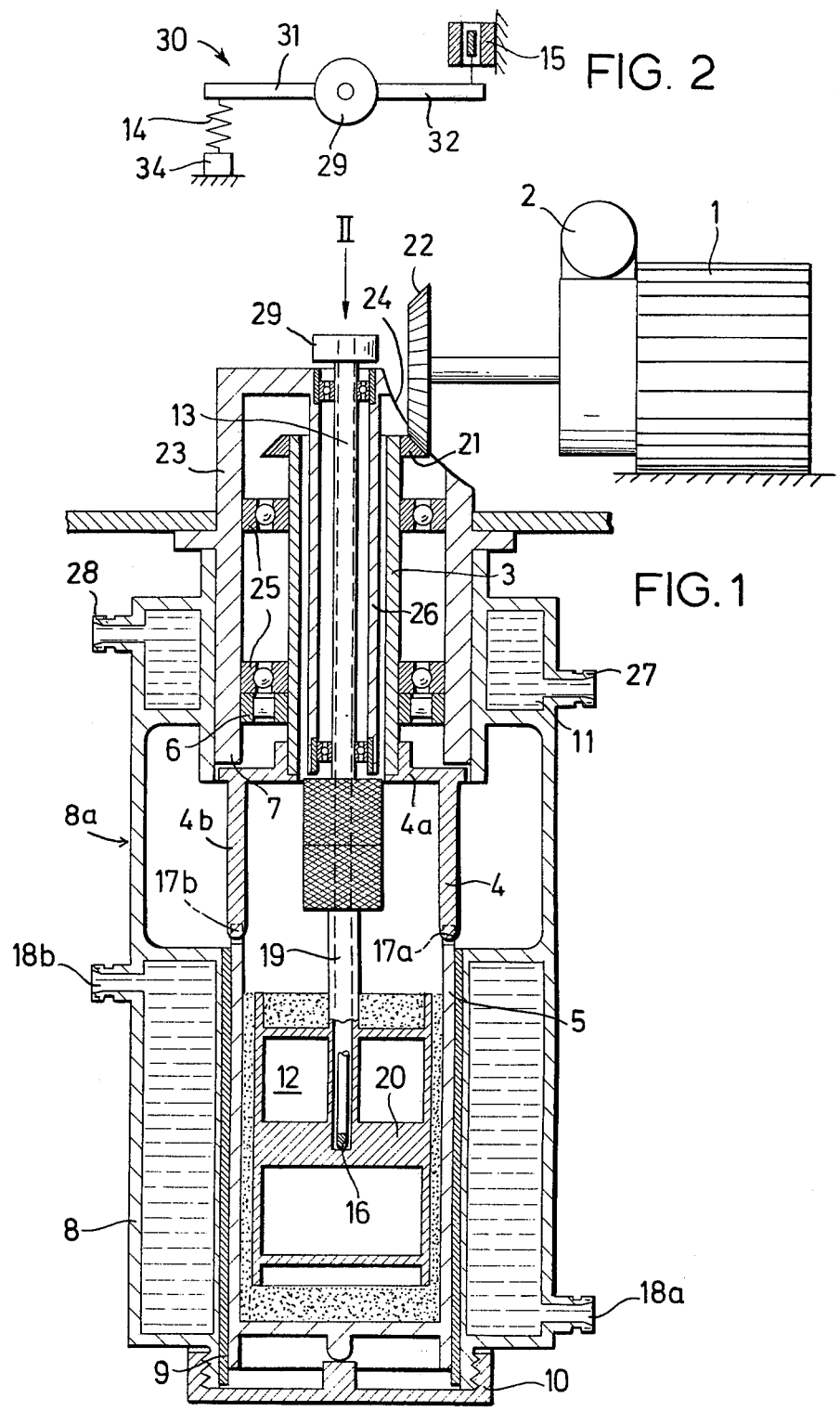

APPARATUS FOR MEASURING VISCOSITY OF LIQUIDS

FIELD OF THE INVENTION

The present invention relates to apparatus for measuring viscosity of liquids and more particularly to rotary viscosimeters of the Couette type or the plate/cone measuring system.

DESCRIPTION OF THE PRIOR ART

In a Couette viscosimeter, the liquid whose viscosity is to be measured is placed in an annular space between two concentrically-disposed cylinders, and the outer cylinder is set in rotation. The torque required to overcome the drag effect of the liquid or the resultant torque applied to the inner cylinder by virtue of the drag effect of the liquid on the inner cylinder is a measure of the viscosity of the liquid. In the plate/cone measuring system, the liquid is placed on a rotating plate and a fixed flat cone, which is placed in contact with the liquid is used as the measuring member. The torque required to overcome the drag effect of the liquid again being a measure of the viscosity thereof.

Since viscosity is a dimension which is highly dependent upon temperature, the temperature of the liquid must be maintained constant. In known rotary viscosimeters, this is done by means of fluid baths, which necessitate complicated constructions and testing procedures. The use of fluid baths is particularly disadvantageous because the outer wall of the outer cylinder is also wetted by fluid of the bath and thus requires additional cleaning once measuring is complete. Moreover, provision must be made for the temperature of the fluid bath to be kept constant automatically.

The object of the present invention is to overcome the disadvantages of the known rotary viscosimeters, particularly with regard to the way in which the temperature of the liquid whose viscosity is being measured is kept constant.

Accordingly the present invention provides apparatus for measuring the viscosity of a liquid comprising a rotatable container means; means for rotating said container means at a desired speed; a freely rotatable member within said container means, said container means and said member defining a volume therebetween for receiving liquid to be measured; a fluid bath surrounding said container means for maintaining said container means at a desired constant temperature; means for measuring torque of said member when said volume is charged with liquid to be measured and said container means is rotated by said rotating means; and a bearing made from a material having a high thermal conductivity and located between and contacting said container means and said fluid bath to facilitate relative rotation therebetween. Preferable the container means is a cylinder.

Such apparatus corresponds to a rotary viscosimeter of the Couette type. In a plate/cone type, the plate is constructed as the front face of an outer cylinder which is so constructed and so disposed, according to the invention, the cone replacing said member.

Dry journal bearing materials having high thermal conductivity are known; examples thereof are dry journal bearing materials with a bronze base, such as sintered bronze, which is filled with polytetrafluorethylene or molybdenum disulphide.

Because of the good thermal conductivity of such bearing bushes, the outer cylinder adopts the temperature of the fluid bath quickly. This fluid bath is preferably closed in apart from the inlet and outlet pipe, by means of which the bath is connected in a recirculatory system.

In order to enable yield limits and moduli of elasticity to be measured, a drive shaft of the outer cylinder is provided with a (free-wheel member) ratchet mechanism which only permits the drive shaft and outer cylinder to turn in one direction. Repelling forces, which the liquid being measured possibly exerts upon the outer cylinder, can therefore not cause a reversal of the rotary movement which would make the measurement inaccurate.

INTRODUCTION TO THE DRAWINGS

The present invention is further described hereinafter, by way of example, with reference to the accompanying drawing, in which:

FIG. 1 is a sectional elevation of a rotary viscosimeter constructed in accordance with the present invention, and FIG. 2 is a view in the direction of the arrow II of FIG. 1 showing a torque-measuring device of the viscosimeter.

FIG. 1 shows a viscosimeter having a drum in the form of an inner cylinder 12 and a container means in the form of an outer coaxial cylinder 5 which is rotatably driven by a drive motor 1 secured to a frame (not shown in the drawings), the drive motor 1 being preferably a regulated direct-current motor and including a tachogenerator (not shown in the drawings). The outer cylinder 5 is coupled to the drive motor 1 by way of a coupling member 4, a hollow shaft 3 and a bevel gear mechanism 2, the hollow shaft 3 being substantially coaxial with the cylinders 5 and 12 and being coupled at its axial end remote from the cylinders 5 and 12 to the gear mechanism 2 by way of a pair of bevel gears 21 and 22.

The coupling member 4 is in the form of an annular plate 4a secured to the end, adjacent the cylinders 5 and 12, of the shaft 3 and carries projections in the form of plugs 4b which extend, preferably parallel with the axis of the outer cylinder 5, and engage in respective slots 17a and 17b in the adjacent end edge of the outer cylinder 5. The plugs 4b are preferably diametrally opposed.

The outer cylinder 5 is mounted in a bore of a substantially annular fluid bath 8 of a housing 8a so as to be coaxial therewith and rotatable relative thereto, the cylinder 5 being journalled in the bath by a dry bearing in the form of a bush 9 comprising, for example a bronze base, such as sintered bronze which is filled polytetrafluorethylene or molybdenum disulphide. The bush 9 allows axial movement of the cylinder 5 to take place, and thus provides a facility for measuring axial forces which act on the outer cylinder 5 during operation of the viscosimeter, such forces being generated with some viscous liquids (Weissenberg effect). Because of the high thermal conductivity of such a bush the temperature of the outer cylinder 5 is maintained at substantially that of the fluid bath 8. The fluid bath 8 is sealed and has an inlet pipe 18a and an outlet pipe 18b which are connected to a thermostatically controlled heat source (not shown in the drawings) and a pump (also not shown in the drawing) which form part of a fluid recirculatory system. A screw cap 10 is provided on one end of the bath 8 and, when fully screwed up, prevents axial movement of the outer cylinder 5 away from the coupling member 4.

The shaft 3 is journalled by bearings 25 in a housing 23 which has an opening 24 into which the bevel gear 22 projects and engages the bevel gear 21.

The inner cylinder 12 is coaxially secured to a rod 13 which extends coaxially through and is rotatably journalled in a sleeve-like projection 26 of the housing 23, which sleeve-like projection 26 extends coaxially within the hollow shaft 3. The rod projects through a central bore in the disc 4a. The cylinder 12 is sealed adjacent both ends to prevent the ingress of the substance being measured.

The rod 13 is preferably hollow and extends into the interior of the cylinder 12 to enable a temperature sensor 16 to be inserted therein to measure the temperature of the cylinder 12. To ensure an accurate measurement of the temperature a disc 20, made of material having a high thermal conductivity, e.g. copper or aluminium, is secured along its periphery to the inner wall of the cylinder 12 by a joint having good thermal conductivity, e.g. a weld or solder joint. Preferably the disc 20 is located at a central point on the axis of the inner cylinder 12.

The rod 13 is secured to the disc 20 and the bore 19 thereof extends into the disc 20 to accommodate the temperature sensor 16 which is preferably in the form of a thermocouple. The sensor 16 thus registers substantially the temperature of the inner cylinder 12.

A cooling jacket 11 of the housing 8a is in secure engagement around the housing 23, cooling fluid e.g. water being pumped through the jacket 11 by way of an inlet 27 and an outlet 28 to maintain the shaft 3 and the rod 13 and the bearings thereof at a reasonable operating temperature e.g. room temperature.

A ratchet mechanism 6 couples the shaft 3 to the housing 23 and allows rotational movement of the shaft 3, and thus the outer cylinder 5, in one direction only. Advantageously the ratchet mechanism 6 has a reversible action.

The torque measuring device shown in FIG. 2 comprises a lever 30 secured to a flange 29 formed on the end, remote from the cylinders 5 and 12, of the rod 13. The lever is divided by the rod 13 into two portions 31 and 32. The portion 31 of the rod 30 is coupled to a bracket 34 secured relative to the housing 23 on a base (not shown in the drawing) by way of a helical spring 14 which maintains the rod 13 in an equilibrium position.

The portion 32 of the rod 31 is connected to an inductive transmitter 15 which provides an indication of the rotational displacement of the rod 13 from the equilibrium position. The transmitter 15 is secured to a base (not shown in the drawings).

In operation, the liquid whose viscosity is to be measured is poured into the annular space between the inner and outer cylinders 12 and 5 so that the fluid covers the cylinder 12. The outer cylinder 5 is then rotationally driven at a preset speed by the motor 1. The resultant drag effect of the liquid on the inner cylinder 12 causes the latter and thus the rod 13 to turn against the restoring force of the spring 14. A measurement of the rotational displacement of the cylinder 12 form its equilibrium position and thus of the viscosity of the liquid is provided by the transmitter 15. The temperature of the liquid whose viscosity is being measured is taken as the average of the temperature of the fluid bath 8 and the sensor 16, since a temperature gradient normally exists across the liquid in a direction radially of the inner cylinder. A further cylinder (not shown in the drawing) may be provided between the outer cylinder 5 and the bush 9 to accommodate tolerances in the internal diameter of the bush 9, the further cylinder being slidable in the bush 9.

The use of a coupling member in the form of the coupling member 4 and the connection of the torque-measuring device to the upper end of the viscosimeter enables the outer cylinder 5 to be quickly and easily removed for emptying and filling with a further liquid and replaced. Alternatively a number of different outer cylinders 5 may be rapidly interchanged to provide quick and easy measurement of viscosity of different liquids.

I claim:

1. Apparatus for measuring the viscosity of a liquid comprising a rotatable container means; means for rotating said container means at a desired speed; a freely rotatable member within said container means, said container means and said member defining a volume therebetween for receiving liquid to be measured; a fluid bath container surrounding said container means having a fluid bath for maintaining said container means at a desired constant temperature; means for measuring torque of said member when said volume is charged with liquid to be measured and said container means is rotated by said rotating means, and a bearing made from a material having a high thermal conductivity and located between and contacting said container means and said fluid bath container to facilitate relative rotation therebetween.

2. The apparatus of claim 1 wherein said container means is a cylinder.

3. The apparatus of claim 2 wherein said bearing comprises a liner coaxial with said cylinder.

4. The apparatus of claim 3 further comprising a coupling member which couples the cylinder to the drive means, one of said cylinder and said coupling member having at least one slot formed therein and the other of said cylinder and said coupling member having a plug engageable in said slot for transmitting rotary drive to said cylinder.

5. The apparatus of claim 4 wherein said slot is formed in said cylinder and said coupling member has said plug.

6. The apparatus of claim 4 further comprising a ratchet mechanism coupling said cylinder and said drive means for allowing rotation of said cylinder in one direction only.

7. The apparatus of claim 6 wherein said ratchet means has reversible action.

8. The apparatus of claim 6 wherein said freely rotatable member comprises a drum.

9. The apparatus of claim 8 wherein said measuring means comprises resilient means for rotationally biassing said drum towards an equilibrium angular position and sensing means for indicating an amount of angular displacement of said drum from said equilibrium position.

10. The apparatus of claim 9 wherein said resilient means is a helical coil spring and said sensing means is an inductive transmitter.

11. The apparatus of claim 2 further comprising a hollow shaft connected to said cylinder and coupled to said drive means by way of a bevel gear mechanism, and a rod projecting substantially coaxially through said shaft and coupling said member to said measuring means.

12. The apparatus of claim 11 wherein said rod has an axial bore extending the length thereof for receiving a temperature sensing means for monitoring the temperature of said member.

13. The apparatus of claim 12 further comprising a cooling jacket surrounding said hollow shaft for maintaining said shaft and said rod below a predetermined temperature.

14. The apparatus of claim 13 further comprising a ratchet mechanism for allowing rotation of said cylinder in one direction only.

15. The apparatus of claim 14 wherein said member is a drum having a disc substantially coaxial with said drum and which is secured along its periphery to the cylindrical wall of said drum, said rod being secured to said disc, said axial bore therein extending into said disc and said disc being formed of a material of high thermal conductivity.

* * * * *